United States Patent
Hall et al.

(10) Patent No.: US 9,927,448 B1
(45) Date of Patent: Mar. 27, 2018

(54) METHOD OF MEASURING FOOD DYES IN BODILY WASTE TO IDENTIFY AND QUANTIFY DRUG CONSUMPTION

(71) Applicants: David R. Hall, Provo, UT (US); Steven Butala, Provo, UT (US); Dan Allen, Springville, UT (US); Daniel Hendricks, Provo, UT (US); Andrew Nguyen, Provo, UT (US); Terrece Pearman, Draper, UT (US)

(72) Inventors: David R. Hall, Provo, UT (US); Steven Butala, Provo, UT (US); Dan Allen, Springville, UT (US); Daniel Hendricks, Provo, UT (US); Andrew Nguyen, Provo, UT (US); Terrece Pearman, Draper, UT (US)

(*) Notice: Subject to any disclaimer, the term of this patent is extended or adjusted under 35 U.S.C. 154(b) by 0 days.

(21) Appl. No.: 15/465,939

(22) Filed: Mar. 22, 2017

(51) Int. Cl.
| | |
|---|---|
| *G01N 33/94* | (2006.01) |
| *G01N 33/493* | (2006.01) |
| *G01N 21/25* | (2006.01) |
| *G01N 33/58* | (2006.01) |

(52) U.S. Cl.
CPC ........... *G01N 33/94* (2013.01); *G01N 21/25* (2013.01); *G01N 33/493* (2013.01); *G01N 33/583* (2013.01); *Y10T 436/13* (2015.01)

(58) Field of Classification Search
CPC .... Y10T 436/13; G01N 33/48; G01N 33/493; G01N 21/31; G01N 21/3103; G01N 21/33; G01N 21/35; G01N 33/94; G01N 21/25
USPC .................. 436/56, 63, 163, 164, 171, 901; 422/82.05, 82.09; 435/29
See application file for complete search history.

(56) References Cited

U.S. PATENT DOCUMENTS

| | | | | |
|---|---|---|---|---|
| 3,341,417 A | * | 9/1967 | Sinaiko | A61K 49/0404 |
| | | | | 116/201 |
| 9,671,343 B1 | * | 6/2017 | Hall | G01N 21/6428 |
| 9,766,257 B1 | * | 9/2017 | Hall | G01N 33/94 |
| 2004/0228802 A1 | * | 11/2004 | Chang | A61K 9/2013 |
| | | | | 424/10.2 |
| 2006/0039865 A1 | * | 2/2006 | Preston | A61K 31/46 |
| | | | | 424/10.4 |
| 2015/0202588 A1 | * | 7/2015 | Allphin | A61K 31/19 |
| | | | | 514/282 |
| 2015/0369794 A1 | * | 12/2015 | Keller | G01N 33/9486 |
| | | | | 435/14 |
| 2016/0109371 A1 | * | 4/2016 | Blair | G01N 21/645 |
| | | | | 436/172 |

FOREIGN PATENT DOCUMENTS

GB          2309166 A  *  7/1997

OTHER PUBLICATIONS

Belaz-David et al. European Journal of Pharmaceutical Sciences, vol. 5, 1997, pp. 335-345.*

* cited by examiner

*Primary Examiner* — Maureen Wallenhorst

(57) ABSTRACT

We disclose a drug tracking system and method of use which may be used to screen a subject's bodily waste and to identify the drug the subject has consumed. The system includes a drug that is tagged with a food dye that may be detected in the subject's bodily waste using absorption spectroscopic analysis. The subject consumes the tagged drug and a user obtains a sample of the subject's bodily waste. The user may analyze the subject's urine using an absorption spectroscopic technique. The user may enter the emission spectrum obtained from the absorption spectroscopic analysis into a database that includes the signature emission spectra from multiple food dyes that are used as drug tags. The emission spectra may be compared and the identity of the food dye and its associated drug may be determined.

11 Claims, 8 Drawing Sheets

METHOD OF MEASURING FOOD DYES IN BODILY WASTE TO IDENTIFY AND QUANTIFY DRUG CONSUMPTION

BACKGROUND

Field of the Invention

This disclosure relates to methods of tracking and identifying pharmaceuticals after consumption, particularly by screening bodily waste for drug markers.

Background of the Invention

The consumption of drugs is largely untracked. This is particularly problematic for dealing with issues such as opiate addiction, sharing of prescriptions, counterfeit drugs, consumption of contraindicated drugs, consumption of multiple drugs with adverse interactions, drug allergies, dosing control and adjustment, emergency medicine and many other situations. It is also difficult to interpret clinical studies when drug compliance of study subjects is inconsistent.

Tracking of drugs in the human waste stream is desirable. Drug tracking molecules that do not have negative physiological effects are also desirable. A drug tracking molecule that is commonly found in food would be an attractive candidate, particularly when it is possible to detect the drug tracking molecule in the human waste stream using noninvasive and well-established analytical methods.

BRIEF SUMMARY OF THE INVENTION

We disclose a drug tracking system which includes a drug tracking tag that may be identified in bodily waste. The drug tracking tag may be a colored molecule commonly used as a food dye which may be measured using absorption spectroscopic analysis techniques. In some embodiments, the food dye may participate in chemical reactions which produce a reaction product. In these embodiments, the reaction product rather than the food dye may be measured in bodily waste.

The food dye may be adhered to or mixed with a drug prior to consumption. The food dye or its reaction product may be measured in urine or other bodily waste to provide a qualitative identification of the drug associated with the food dye. In some embodiments, the signal from the absorption spectroscopic analysis may be normalized to a urine metabolite or urine specific gravity to provide a quantitative assessment of drug consumption.

Each food dye may be associated with a unique drug. Therefore, the emission spectra produced by analyzing a subject or patient's bodily waste may provide conclusive evidence of the identity of the consumed drug.

The drug tracking system may include a database which stores multiple signature emission spectra (spectral signatures) of the food dyes used as drug tags. Computer readable code which may be associated with the database may compare the emission spectrum from the analysis of the subject's bodily waste with the signature emission spectra of the various food dyes. When a match is made, the food dye, and consequently, its associated drug may be identified.

In some embodiments, the absorption spectroscopic analysis of the bodily waste sample may be conducted using a range of excitation wavelengths. In some embodiments, one or more follow-up absorption spectroscopic analyses may be conducted, each using a single excitation wavelength. Each single excitation wavelength may be calculated from a maximal emission wavelength associated with a peak from the emission spectrum obtained from the first absorption spectroscopic analysis. Each peak may represent a different food dye. The follow-up absorption spectroscopic analysis may provide more conclusive identification of the tagged drugs by creating an emission spectrum that removes overlapping signals.

In embodiments in which the bodily waste is urine, the data from the absorption spectroscopic analysis may be normalized to either a urine analyte or urine specific gravity. This may provide more quantitative data in addition to merely qualitatively identifying the drug the subject or patient has consumed.

DETAILED DESCRIPTION OF THE INVENTION

Definitions

Figure 1:
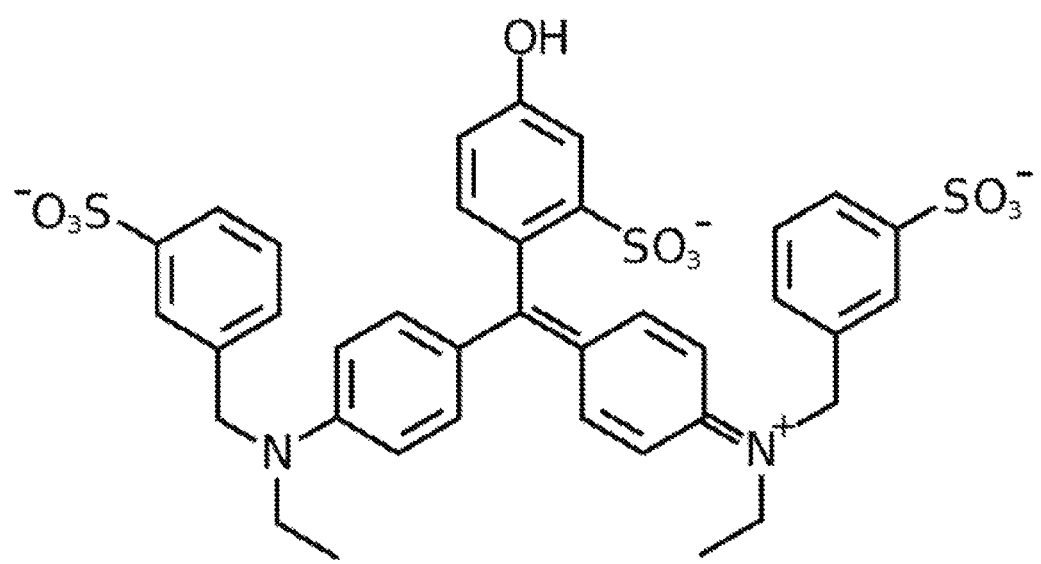
FIG. 1 shows the chemical structure of the food dye, green number 3.

Drug, as used herein, means any pharmacologically active agent or mixture of agents.

Drug consumption, as used herein, means taking a drug into the body through any method of administration.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a drug tracking system which includes a method of tracking drug consumption by a subject or patient. One advantage of the disclosed drug tracking system is that the disclosed method does not require a technique to measure the drug or its metabolite directly. Rather the method detects colored molecules which may commonly be used as food dyes which are used as a tag for the drug. A different food dye may be used to tag each drug. The food dye may be applied to the drug by spraying or painting the food dye on the drug, mixing the food dye with the drug, or other methods known in the art. Each tagged drug may be associated with a different food dye. Each food dye may have a different absorption and emission spectrum. While the drug may separate from the food dye after consumption, the excreted food dye in bodily waste is still indicative of consumption of the particular defined drug.

Another advantage of the disclosed drug tracking system is that the food dye may be detected in bodily waste, including urine, using well-established absorption spectroscopic techniques. In some embodiments, the absorption spectroscopic analysis may be conducted by analytical equipment that is housed within a medical toilet. In this embodiment, the food dye may be detected in a convenient and unobtrusive matter. The subject or patient simply urinates or defecates normally into the bowl of the medical toilet and the spectrometer within the medical toilet measures the food dye.

In some embodiments, the absorption spectroscopic analysis of the urine or feces sample includes exposing the urine sample to an energy source that emits a range of excitation wavelengths. The range of excitation wavelengths may span one or more of the infrared, ultraviolet, or visible light ranges. For example, those dyes which are detectable within the visible range, the excitation wavelengths may be between 390 nm and approximately 700 nm.

Some examples of food dyes which may be used as drug trackers in the disclosed system include, but are not limited to, green number 3, red number 3, methylene blue, indigo carmine, cochineal carmine red, and tartrazine. While some food dyes do not participate in metabolism or other chemical reactions under conditions to which the drug and food dye are likely to be exposed, other food dyes form one or more reaction products. For example, red number 3, methylene blue, and cochineal carmine red may be converted to reaction products which may be measured in bodily waste to indicate drug consumption. The reaction product may require different conditions for detection using absorption spectroscopic analysis than the original food dye. For example, methylene blue is a blue colored dye that may be detected using an excitation wavelength of about 668 nm. However, its reaction product is leucomethylene which is colorless and detectable using an excitation wavelength of about 246 nm. Consequently, the absorption spectroscopic analysis used to detect a drug tagged with methylene blue may include excitation wavelengths that include both 668 nm and 246 nm.

Some food dyes change their spectroscopic properties with changes in the pH. For example, indigo carmine changes colors with change in pH. Accordingly, it may be useful to adjust the pH of the sample of urine or other bodily waste prior to analysis.

As a result of the absorption spectroscopic analysis, the system produces an emission spectrum. The emission spectrum may be entered into a database which stores the signature emission spectra (spectral signatures) from multiple food dyes which may be used as drug tags. A computer readable medium which may associated with the database may compare the emission spectra produced from the absorption spectroscopic analysis of the bodily waste with the signature emission spectra of the food dyes stored in the database. When a match between the emission spectra from the absorption spectroscopic analysis of the bodily waste and the signature emission spectra in the database is made, the drug associated with the food dye that produces the signature emission spectra may be identified. In some embodiments, the drug identified using the drug tracking system may be compared to a list of medications which have been prescribed to the subject or patient. The user may therefore confirm whether the subject or patient has consumed the proper medications. This may be useful for patient care and in clinical trials where a clinical researcher needs to know whether the subject was compliant with taking the study medication. The method may also be useful to keep clinical researchers blind as to which subjects received the drug and which received placebo. The food dye may be measured by a technician who is not part of the clinical trial so as not to bias the study.

In some embodiments, the first absorption spectroscopic analysis, which may be conducted using a range of excitation wavelengths, may produce an emission spectrum with one or more peaks at certain emission wavelengths. One or more follow-up absorption spectroscopic analysis may then be conducted on the same sample. The follow-up absorption spectroscopic analysis may include a single excitation wavelength that may be calculated to be the maximum excitation wavelength which resulted in the peak shown on the emission spectrum. A follow-up absorption spectroscopic analysis may be performed for each peak in the emission spectrum. The one or more follow-up absorption spectroscopic analyses may provide clearer spectroscopy data without overlapping peaks, particularly when the subject has consumed more than one drug that has been tagged with a different food dye. The emission spectra may then be entered into the database, compared to signature emission spectra of a variety of food dyes that are used as drug tags. The one or more drugs the subject has consumed may then be identified by determining the one or more drugs associated with the matching emission spectra.

Urine from a subject or patient may be more or less dilute depending on the hydration status of the subject or patient. Consequently, it may be useful to normalize the signal obtained from measuring a food dye or its reaction product (which may be area under the curve or height of the emission peak) to produce more quantitative data. For example, a urine metabolite may be used to normalize the signal from the emission spectra. Alternatively, urine specific gravity may be used to normalize the spectroscopy data.

Figure 2:
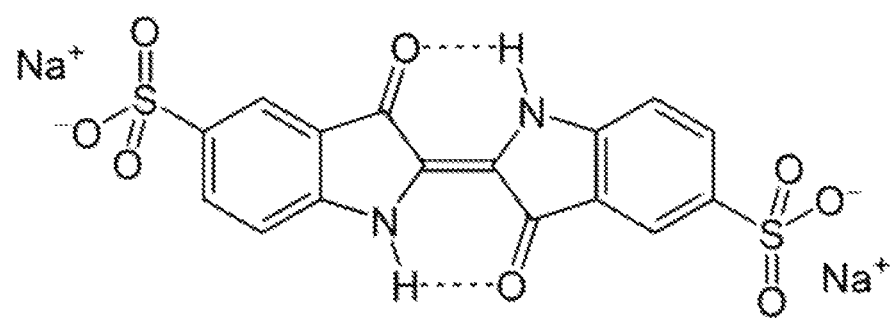
FIG. 2 shows the chemical structure of the food dye, indigo carmine.
Figure 3:
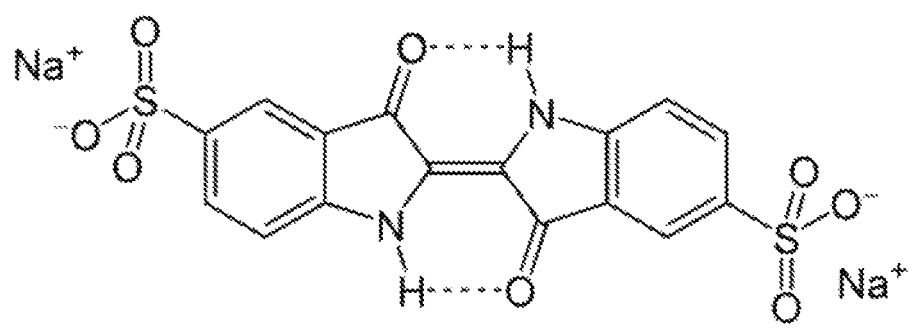
FIG. 3 shows the chemical structure of the food dye, tartrazine.
Figure 4:
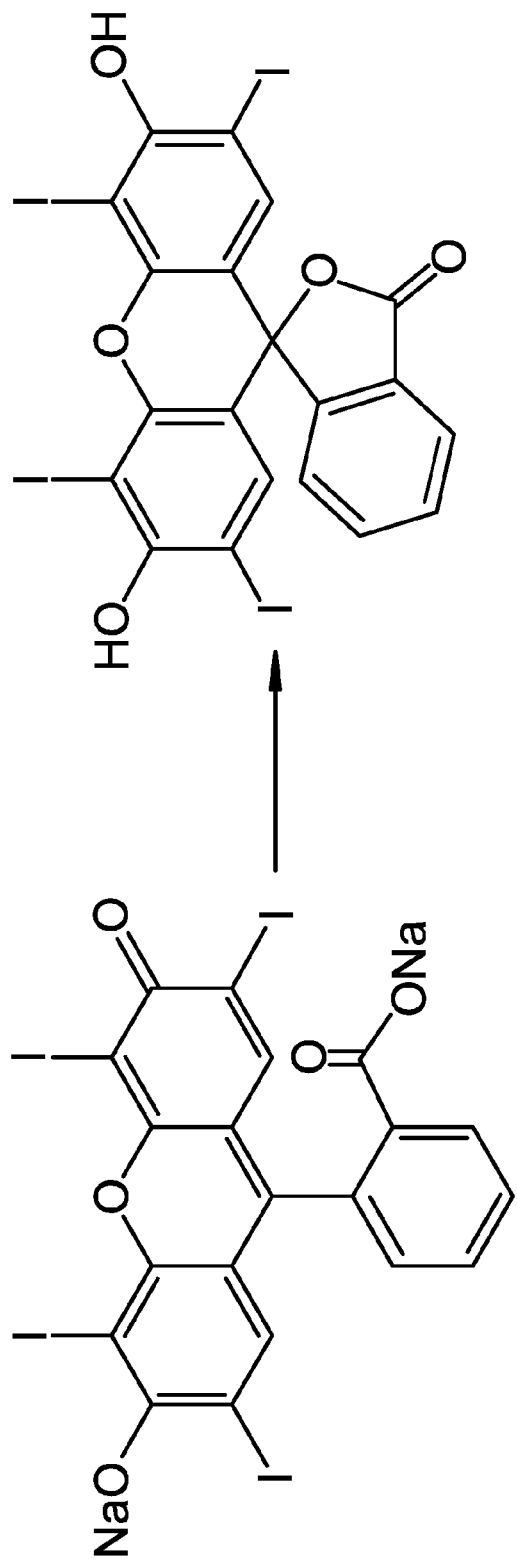
FIG. 4 shows the chemical structure of the food dye, red number 3 and its reaction product.
Figure 5:
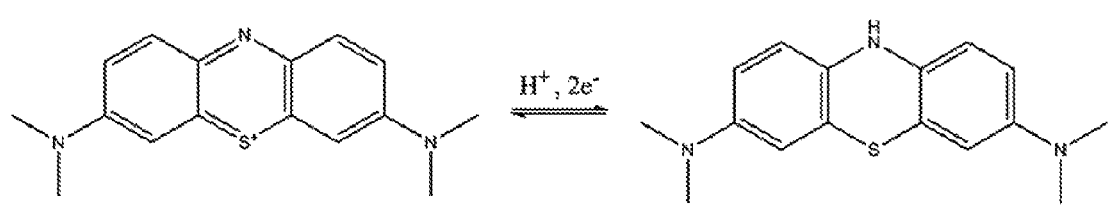
FIG. 5 shows the chemical structure of the food dye, methylene blue and its reaction product, leucomethylene blue.
Figure 6:
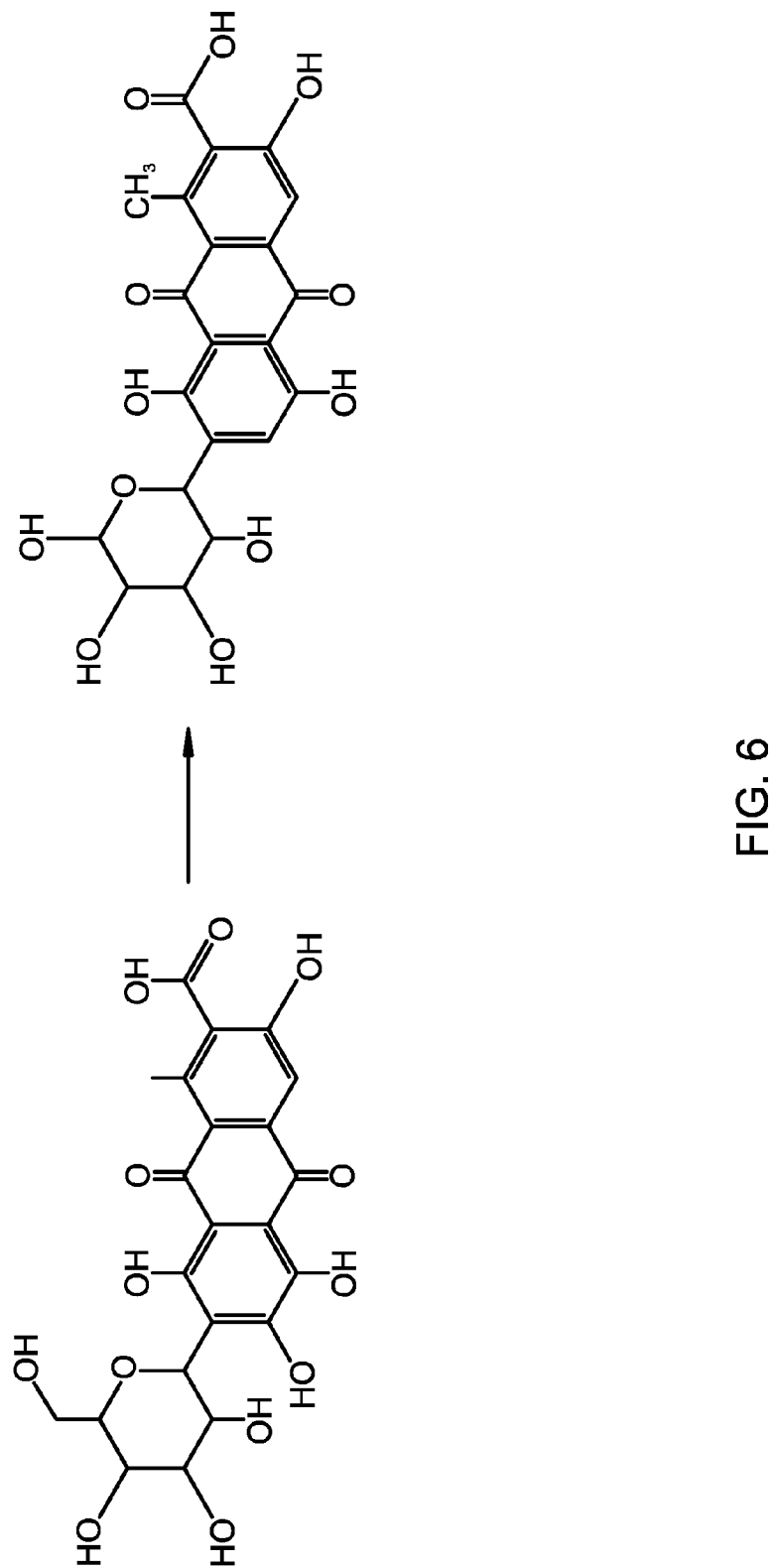
FIG. 6 shows the chemical structure of the food dye cochineal carmine red and its reaction product.

Referring now to the drawings, FIG. 1-6 include the chemical structures of food dyes which may be used as drug tags according to the disclosure. FIGS. 4-6 also show reaction products of the food dyes which may be detected in urine to indicate consumption of the drug that was tagged with the food dye.

FIG. 1 shows the chemical structure of the common food dye, green number 3. Green number 3 is not known to be metabolized. Therefore, green number 3 may be used as a drug tracking molecule and measured in urine directly. Green number 3 has a peak absorption wavelength of about 625 nm which is within the visible range.

FIG. 2 shows the chemical structure of the common food dye, indigo carmine. Indigo Carmine is excreted mostly intact. However, the color, and therefore, the absorption spectra, of indigo carmine is pH dependent. Therefore, it may be useful to adjust the pH of the urine sample prior to measuring indigo carmine according to an embodiment of the disclosure. Indigo carmine has a peak absorption wavelength of about 609 nm, within the visible range.

FIG. 3 shows the chemical structure of the common food dye, tartrazine, also known as FD&C Yellow 5 and E102. Tartrazine has a peak absorption wavelength in aqueous solution of about 425 nm, within the visible range. Metabolism of tartrazine depends on the route of administration. Tartrazine is excreted unchanged when administered intraperitoneally. Oral administration results in about half of the tartrazine dose is converted to sulphanilic acid by intestinal microflora although very little sulphanilic acid is excreted in urine after tartrazine consumption.

FIG. 4 shows the chemical structure of the common food dye, red number 3, also known as erythrosine, and its reaction product. Red dye number 3 has a peak absorption wavelength of about 530 nm, within the visible range.

FIG. 5 shows the chemical structure of methylene blue and its reaction product, leucomethylene blue. Methylene blue is a blue colored dye with a peak absorption wavelength of about 664 nm. It becomes reversibly reduced to leucomethylene blue which is colorless. Leucomethylene blue has a peak absorption wavelength of about 246 nm, which is outside the visible range but readily detectable with spectrophotometric methods using excitation wavelengths in the ultraviolet range.

FIG. 6 shows the chemical structure of cochineal carmine red and its metabolite. Cochineal carmine red has a peak absorption wavelength of about 513 nm, within the visible range. Conchineal carmine red is excreted both in the urine and feces.

Figure 7:
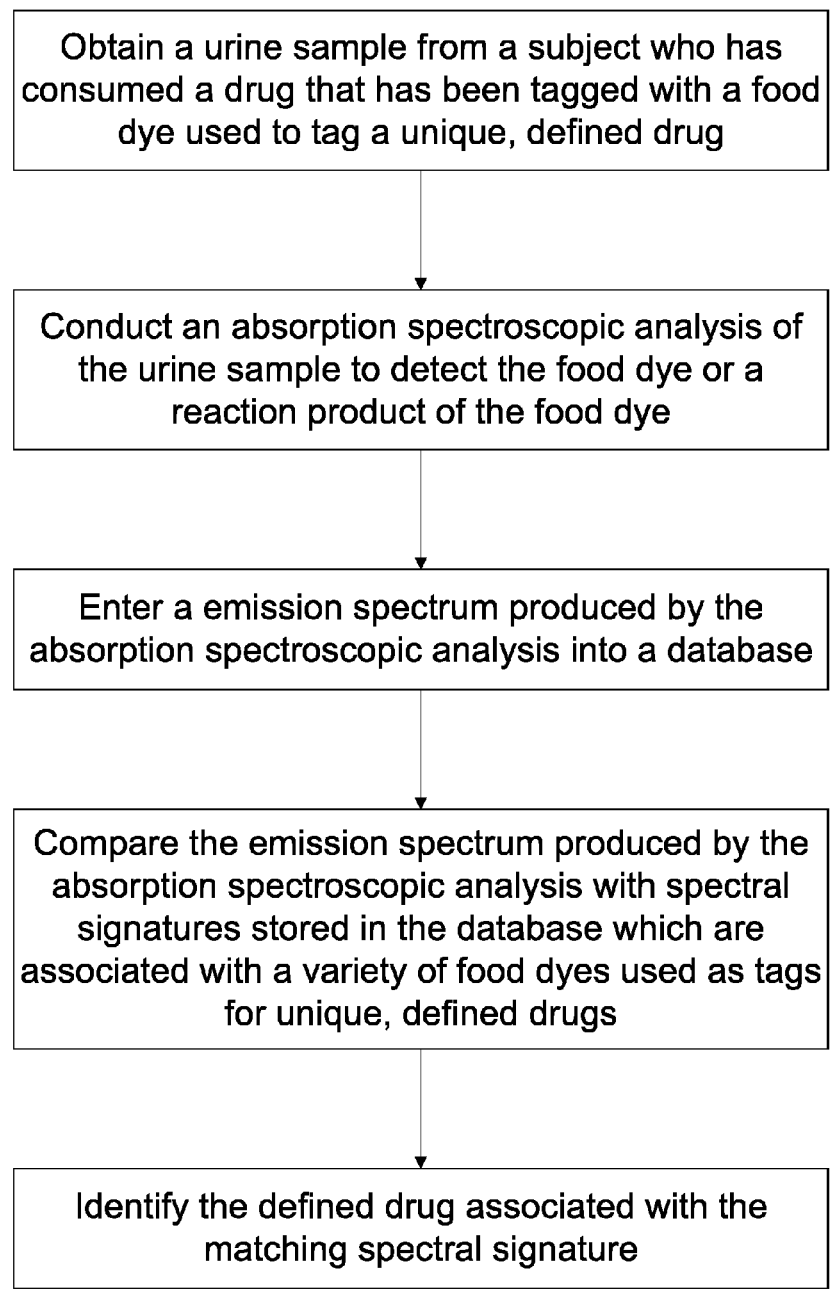
FIG. 7 provides a flow chart which includes steps in an embodiment of a method of using the disclosed drug tracking system.

FIG. 7 presents a flow chart describing a method of using food dyes in a drug tagging system as disclosed herein. A subject first consumes a drug that has been tagged with a food dye. The food dye is used as a tag only for the drug the subject has consumed. The food dye or its reaction product may be detected in the subject's urine using an absorption spectroscopic technique. A user then obtains a sample of the subject's urine and analyzes the urine using an absorption spectroscopic technique. The absorption spectroscopic technique uses a range of multiple excitation wavelengths and produces an emission spectrum which has a peak representing a maximum emission wavelength. The user enters the emission spectrum into a database in which the emission spectra of multiple food dyes that are used as drug tags are stored. These emission spectra represent the signature emission spectra of the food dyes. The database also includes the identity of the drug which is tagged with the food dye associated with the signature emission spectra. Using computer readable medium associated with the database, the user compares the emission spectrum with the signature emission spectra in the database and finds a match. The user then determines which drug is associated with the food dye that has the matching signature emission spectra. This information is also stored in the database.

Figure 8:
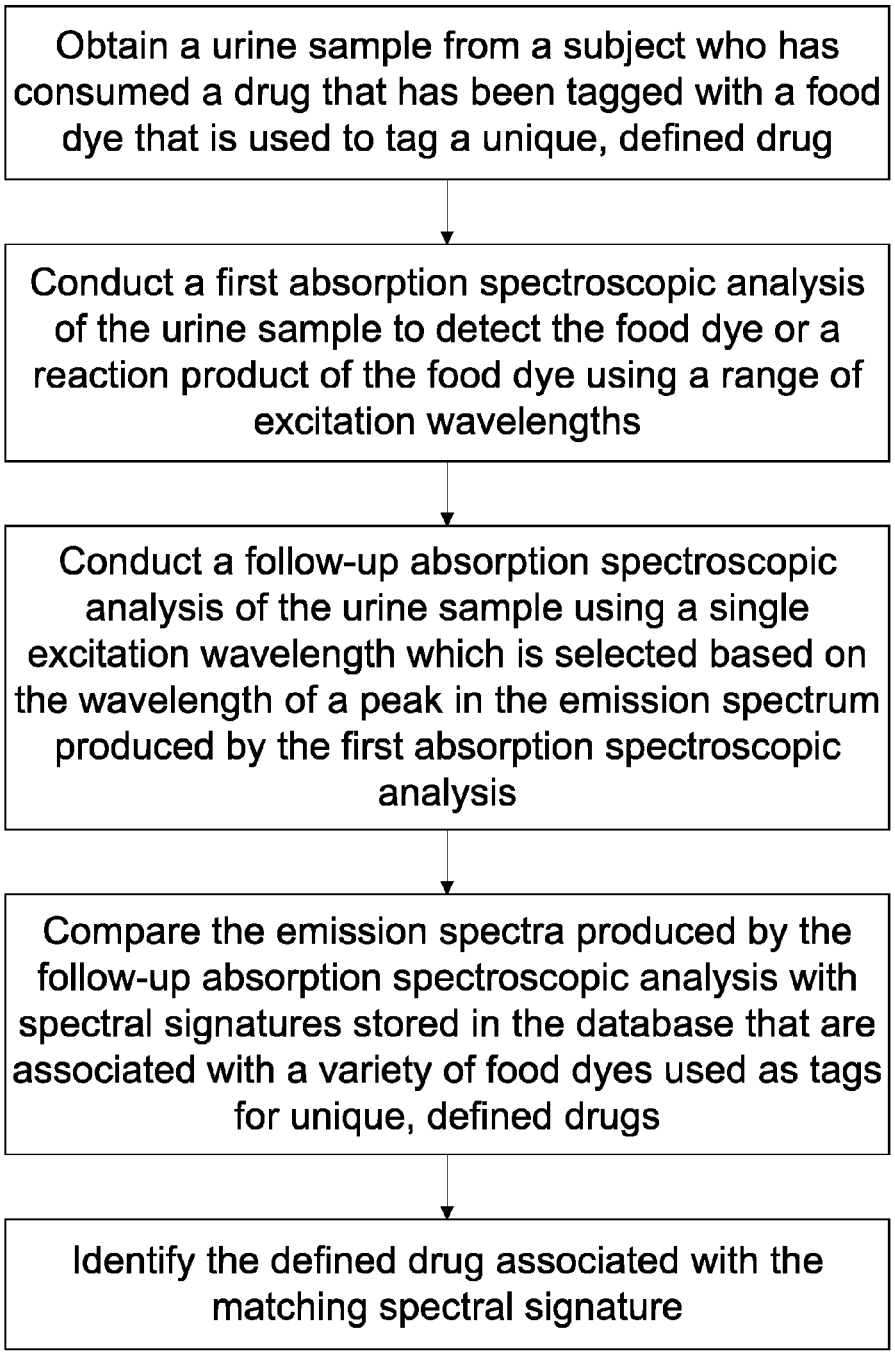
FIG. 8 provides a flow chart which includes steps in an embodiment of a method of using the disclosed drug tracking system.

FIG. 8 presents a flow chart in which a follow-up spectral analysis is used to confirm the identity of the food dye and, consequently, the associated drug. The method begins as the method described in FIG. 7 with a subject consuming a drug that has been tagged with a food dye according to the disclosure. A user then obtains a sample of the subject's urine and analyzes the urine using an absorption spectroscopic technique. The absorption spectroscopic technique uses a range of multiple excitation wavelengths and produces an emission spectrum which has a peak representing a maximum emission wavelength. The urine is then analyzed by conducting a follow-up absorption spectroscopic analysis. The follow-up absorption spectroscopic uses a single excitation wavelength. The single excitation wavelength is calculated based on the wavelength of the peak in the emission spectrum. The emission spectrum that results from the follow-up absorption spectroscopic analysis may include less background from other components in the urine thereby confirming the wavelength of the peak associated with the food dye. A separate follow-up absorption spectroscopic analysis may be conducted using single wavelengths extrapolated from an additional peak in the first emission spectrum. Consequently, the identity of an emission peak resulting from a second food dye associated with a second drug may be confirmed. The one or more follow up spectra may then be entered into the database, compared to signature emission spectra of food dyes used as drug tags, and the identity of their associated drugs revealed.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of tracking drug consumption comprising the steps of:
   obtaining a urine sample from a subject who has consumed a drug, wherein the drug has been tagged with a food dye, wherein the food dye or a reaction product of the food dye is detectable by an absorption spectroscopic analysis of the urine sample; wherein the food dye is exclusively used to tag a single defined drug;
   conducting a first absorption spectroscopic analysis of the urine sample to detect the food dye or the reaction product of the food dye;
   conducting at least one follow-up absorption spectroscopic analysis of the urine sample, wherein the at least one follow-up spectroscopic analysis comprises the step of exposing the urine sample to a single excitation wavelength, wherein the single excitation wavelength is selected based on a wavelength of a peak in an emission spectrum that is produced by the first absorption spectroscopic analysis of the urine sample, wherein the first absorption spectroscopic analysis comprises the step of exposing the urine sample to a first energy source, and wherein the first energy source emits a range of excitation wavelengths.

2. The method of claim 1, wherein the food dye consists of green number 3, wherein the single excitation wavelength is about 625 nm.

3. The method of claim 1, wherein the food dye consists of red number 3, wherein the single excitation wavelength is about 530 nm.

4. The method of claim 1, wherein the food dye consists of methylene blue, wherein the single excitation wavelength is about 668 nm.

5. The method of claim 1, wherein the food dye consists of indigo carmine, wherein the single excitation wavelength is about 609 nm.

6. The method of claim 1, wherein the food dye consists of cochineal carmine red, wherein the single excitation wavelength is about 513 nm.

7. The method of claim 1, wherein the food dye consists of tartrazine, wherein the single excitation wavelength is about 425 nm.

8. The method of claim 1, wherein the reaction product of the food dye consists of leucomethylene blue, wherein the single excitation wavelength is about 246 nm.

9. The method of claim 1, wherein the food dye comprises indigo carmine, and further comprising the step of adjusting a pH value of the urine sample to an optimal level for measuring a peak absorption wavelength of the food dye.

10. A method of tracking drug consumption comprising the steps of:
  obtaining a urine sample from a subject who has consumed a drug, wherein the drug has been tagged with a food dye, wherein the food dye or a reaction product of the food dye is detectable by an absorption spectroscopic analysis of the urine sample; wherein the food dye is exclusively used to tag a single defined drug;
  conducting a first absorption spectroscopic analysis of the urine sample to detect the food dye or the reaction product of the food dye;
  measuring a concentration of a urine metabolite in the urine sample; and
  normalizing a height of a peak within an emission spectrum with the concentration of the urine metabolite in the urine sample, wherein emission spectrum is produced by the first absorption spectroscopic analysis of the urine sample.

11. A method of tracking drug consumption comprising the steps of:
  obtaining a urine sample from a subject who has consumed a drug, wherein the drug has been tagged with a food dye, wherein the food dye or a reaction product of the food dye is detectable by an absorption spectroscopic analysis of the urine sample; wherein the food dye is exclusively used to tag a single defined drug;
  conducting a first absorption spectroscopic analysis of the urine sample to detect the food dye or the reaction product of the food dye;
  measuring specific gravity of the urine sample; and
  normalizing a height of a peak within an emission spectrum with a measurement of specific gravity of the urine sample, wherein the emission spectrum is derived from the first absorption spectroscopic analysis of the urine sample.

* * * * *